US007993870B2

(12) United States Patent
Ewert et al.

(10) Patent No.: US 7,993,870 B2
(45) Date of Patent: *Aug. 9, 2011

(54) EARLY DETECTION OF PATHOGENS IN BLOOD

(75) Inventors: Matt Ewert, St. Petersburg, FL (US); Philip Amuso, Tampa, FL (US); Andrew Cannons, Tampa, FL (US)

(73) Assignee: University of South Florida, Tampa, FL (US)

( * ) Notice: Subject to any disclaimer, the term of this patent is extended or adjusted under 35 U.S.C. 154(b) by 27 days.

This patent is subject to a terminal disclaimer.

(21) Appl. No.: 12/416,775

(22) Filed: Apr. 1, 2009

(65) Prior Publication Data
US 2009/0305383 A1    Dec. 10, 2009

Related U.S. Application Data

(62) Division of application No. 10/604,779, filed on Aug. 15, 2003.

(60) Provisional application No. 60/319,474, filed on Aug. 15, 2002, provisional application No. 60/319,803, filed on Dec. 19, 2002.

(51) Int. Cl.
*C12Q 1/68* (2006.01)
*C12Q 1/54* (2006.01)
*C12Q 1/02* (2006.01)

(52) U.S. Cl. ............................ 435/29; 435/6.15; 435/14
(58) Field of Classification Search ........................ None
See application file for complete search history.

(56) References Cited

U.S. PATENT DOCUMENTS
4,693,972 A    9/1987    Mansour et al.

FOREIGN PATENT DOCUMENTS
WO    WO 02/090539    11/2002

OTHER PUBLICATIONS

Faux, S. P. et al. "Calcium chelator Quin-2 prevents crocidolite-induced DNA strand breakage in human white blood cells" *Mutation Research*, 1994, pp. 209-215, vol. 311.
Titball, R. W. "Bacterial Phospholipases C" *Microbiological Reviews*, Jun. 1993, pp. 347-366, vol. 57, No. 2.
Polymerase Chain Reaction for Rapid Diagnosis of Candidemia; *Bull Acad Mil Med Science*; Sep. 1998, vol. 22, No. 3.
Al-Soud et al.; Purification and Characterization of PCR-inhibitory Components in Blood Cells; *Journal of Clinical Microbiology*; p. 485-493; Feb. 2000.
Archibald et al.; Comparison of BACTEC MYCO/F LYTIC and WAMPOLE Isolator 10 (Lysis-Centrifugation) . . . ; *Journal of Clinical Micro.*; p. 2994-2997; Aug. 2000.

Bernhardt et al.; Detection of Bacteria in Blood by Centrifugation and Filtration; *Journal of Clinical Microbiology*; p. 422-425; Mar. 1991.
Brannon et al.; Clinical Comparison of Lysis-Centrifugation and Radiometric Resin Systems for Blood Culture; *Journal of Clinical Microbiology*; p. 886-887; Nov. 1986.
Cao et al.; The Purification and Characterization of a Phospholipase A in Hamster Heart . . . ; *Journal of Biological Chemistry*; vol. 262, No. 35; p. 16927-16935; Dec. 15, 1987.
Cassels et al.; The Interaction of Streptokinase-Plasminogen Activator Complex, Issue-Type Plasminogen Activator, Urokinase and Their Acylated . . . ; Journal of Biochem; p. 395-400; 1987.
Castellino; Biochemistry of Human Plasminogen; Seminars in Thrombosis & Hemostasis; vol. 10, No. 1; 1984.
Chen et al.; 1-Cys Peroxiredoxin, a Bifunctional Enzyme with Glutathione Peroxidase and Phospholipase A2 Activities; *Journal Biological Chemistry*; vol. 275; p. 28421-28427; Sep. 2000.
Siersema et al.; Blood Culture Bottles are Superior to Lysis-Centrifugation Tubes for Bacteriological Diagnosis . . . ; *Journal of Clinical Microbiology*; p. 667-669; Mar. 1992.
Hamilton et al.; Effect of Delay in Processing on Lysis-Centrifugation Blood Culture Results from Marrow Transplant Patients; *Journal of Clinical Microbiology*; p. 1588-1593; Jul. 1989.
Hoffman et al.; Bone Marrow Aspirate Culture Superior to Streptokinase Clot Culture and 8 ML 1:10 Blood-To-Broth . . . ; *American Society of Tropical Medicine & Hygiene*; p. 836-839; 1986.
Morata et al.; Diagnostic Yield of a PCR Assay in Focal Complications of Brucellosis; *Journal of Clinical Microbiology*; p. 3743-3746; Oct. 2001.
Li et al.; Effects of Volume and Periodicity on Blood Cultures; *Journal of Clinical Microbiology*; p. 2829-2831; Nov. 1994.
Klevezas et al.; Single-Step PCR for Detection of *Brucella* spp. from Blood and Mild of infected Animals; *Journal of Clinical Microbiology*; p. 3087-3090; Dec. 1995.
Ortuno et al.; Rapid Diagnosis of Human Brucellosis by Peripheral-Blood PCR Assay; *Journal of Clinical Microbiology*; p. 2927-2930; Nov. 1997.
Queipo-Ortuno et al.; Rapid Diagnosis of Human Brucellosis by Peripheral-Blood CRR Assay; *Journal of Clinical Microbiology*; P9. 2927-2930; Nov. 1997.
Gamboa et al.; Detection and Identification of Mycobacteria by Amplification of RNA and DNA in Pretreated Blood and Bone . . . ; *Journal of Clinical Microbiology*; p. 2124-2128; Aug. 1997.

(Continued)

*Primary Examiner* — Lisa Hobbs
(74) *Attorney, Agent, or Firm* — Saliwanchik, Lloyd & Eisenschenk

(57) ABSTRACT

The present invention is a method of extracting infectious pathogens from a volume of blood including the steps of creating a fibrin aggregate confining the pathogens and introducing a fibrin lysis reagent to expose the pathogens for analysis. The fibrin lysis reagent is preferably composed of plasminogen and streptokinase frozen in coincident relation until the fibrin lysis reagent is needed whereby streptokinase enzymatically reacts with plasminogen to form plasmin upon thawing. The plasminogen is suspended in an aqueous salt solution prior to freezing including NaCl and $Na_3PO_4$.

17 Claims, 20 Drawing Sheets

OTHER PUBLICATIONS

Morata et al.; Posttreatment Follow-Up of Brucellosis by PCR Assay; *Journal of Clinical Microbiology*; p. 4163-4166; Dec. 1999.

Miles et al.; Binding and Activation of Plasminogen on the Platelet Surface; *Journal of Biological Chemistry*; vol. 260, No. 7; p. 4303-4311; Apr. 1985.

Gaffney et al.; Plasma Fibrinogen and its Fragments During Streptokinase Treatment; *British Journal of Haematology*; 1974.

Malin et al.; Effect of Tetrahydropyrimidine Derivatives on Protein-Nucleic Acids Interaction; *Journal of Biological Chemistry*; vol. 274; p. 6920-6929; Mar. 12, 1999.

Malin et al.; Induction of Synthesis of Tetrahydropyrimidine Derivatives in *Steptomyces* Strains and Their Effect on *Escherichia coli.*; *Journal of Bacteriology*; p. 385-395; Jan. 1996.

Phospholipase A2 from Bee Venom; *Methods in Enzymology*, vol. 71; 1981.

Nguyen et al.; Thrombolysis Using Liposomal-Encapsulated Streptokinase: An In Vitro Study; vol. 192; *P.S.E.B.M.*; 1989.

Birnboim, H.C.; Rapid Extraction of High Molecular Weight RNA from Cultured Cells & Granulocytes for Northern Analysis; *Nucleic Acids Research*; vol. 16, No. 4; 1988.

Fisher et al.; Lysosomal-type PLA2 & Turnover of Alveolar DPPC; Lung Cellular & Molecular Physiology; vol. 280; p. 74-754; Apr. 2001.

Shipolini et al.; Phospholipase A from Bee Venom; *Journal Biological Chemistry*; p. 459-468; 1971.

Menashe et al.; Hydrolysis of Dipalmitoylphosphatidylcholine Small Unilamellar Vesicles by Porcine Pancreatic . . . ; *Journal of Biological Chemistry*; vol. 261, No. 12; p. 5328-5333; 1986.

Molloy et al.; Proteomic Analysis of the *Escherichia coli* Outer Membrane; *Journal of Biological Chemistry*; p. 2871-2881; 2000.

Sponer et al.; Electronic Properties, Hydrogen Bonding, Stacking, and Cation Binding of DNA and RNA Bases; Institute of Biophysics; Aug. 2001.

Gonzalez et al.; Mechanism of Action of Polymeric Aurintricarboxylic Acid, a Potent Inhibitor of Protein-Nucleic Acid Interactions; *American Chemical Society*; 1980.

Oberbaumer et al.; Detection of RNA on Northern Blots by Negative Staining with Aurinlricarboxylic Acid; *Journal Biochemistry*; p. 77-79; 1990.

Givens et al.; Inhibition of RNA-directed DNA Polymerase by Aurintricarboxylic Acid; Nucleic Acids Research; vol. 3, No. 2; Feb. 1976.

Hallick et al.; Use of Aurintricarboxylic Acid as an Inhibitor of Nucleases During Nucleic Acid Isolation; Nucleic Acids Research; vol. 4, No. 9; Sep. 1977.

Guo et al.; Aurin Tricarboxylic Acid Directly Activates Platelets; Thrombosis Research; p. 77-88; 1993.

Gonzalez et al.; Fractionation and Structural Elucidation of the Active Components of Aurintricarboxylic Acid, A Potent Inhibitor of Protein Nucleic Acid . . . ; *Biomedical Press*; 1979.

Skidmore et al.; Characterization and Use of the Potent Ribonuclease Inhibitor Aurintricarboxylic Acid for the Isolation of RNA..*Journal of Biological Chemistry*; p. 73-80; 1989.

Tsutsui et al.; Fractionation of Aurintricarboxylic Acid & Effects of its Components on Nuclear Swelling & Nucleic Acid Synthesis; *Biomedical Press*; p. 14-23; 1978.

Nakane et al; Differential Inhibition of Various Deoxyribonucleic Acid Polymerases by Evans Blue & Aurintricarboxylic Acid; *Journal of Biological Chemistry*; p. 91-96; 1988.

Rozalski et al.; Effects of Fibrinogen Receptor Antagonist GR144053F & Aurintricarboxylic Acid on Platelet Activation and Degranulation; *Biochemical Pharmacology*; p. 1399-1408; 2001.

Browne et al.; Binding Studies of Cationic Thymidyl Deoxyribonucleic Guanidine to RNA Homopolynucleotides; Jul. 1995.

Huang et al.; Electric Manipulation of Bioparticles and Macromolecules on Microfabricated Electrodes; *Analytical Chemistry*; vol. 73, No. 7; Apr. 1, 2001.

Cheng et al.; Isolation of Cultured Cervical Carcinoma Cells Mixed with Peripheral Blood Cells on a Bioelectronic Chip; *Analytical Chemistry*; vol. 70, No. 11; Jun. 1, 1998.

Li et al.; Transport, Manipulation, and Reaction of Biological Cells On-Chip Using Electrokinetic Effects; *Analytical Chemistry*; vol. 69, No. 8; Apr. 15, 1997.

Yang et al.; Granted, Stacked Microlaboratory for Biological Agent Detection with DNA & Immunoassays; *BioSensors & BioElectronics*; p. 605-618; 2002.

Edman et al; Electric Field Directed Nucleic Acid Hybridization on Microchips; *Nucleic Acids Research*; vol. 25, No. 24; 1997.

Ewalt et al; Detection of Biological Toxins on an Active Electronic Microchip; Analytical Biochemistry; p. 162-172; 2001.

Forster et al.; A Laminated, Flex Structure for Electronic Transport & Hybridization of DNA; *BioSensors & BioElectronics*; p. 187-194; 2001.

Boom et al.; Rapid and Simple Method for Purification of Nucleic Acids; Journal of Clinical Microbiology; vol. 28, No. 3; p. 495-503.

Bruisten et al.; Stability of HIV-1 RNA in Blood During Specimen Handling and Storage Prior to Amplification by NASBA-QT; *Journal of Biological Methods*; p. 199-207; 1997.

Read, S.J.; Recovery Efficiencies of Nucleic Acid Extraction Kits as Measured by Quantitative LightCycler PCR; Journal of Clinical Pathol; p. 86-90; 2001.

Zhang et al., Detection of *Streptococcus pneumoniae* in Whole Blood by PCR. *J Clin Microbiol*, 1995, pp. 596-601, vol. 33.

Cassels et al., The Interaction of Streptokinase/plasminogen Activator Complex, Tissue-type Plasminogen Activator, Uurokinase and Their Acylated Derivatives with Fibrin and Cyanogen Bromide Digesto f Fibrinogen. *Biochem*, 1987, J 247:395-400.

Dupe et al., The Evaluation f Plasmin and Streptokianse Activator Complexes in a New Rabbit Model of Venous Thrombosis. *Thrombos Haemostas*, 1981, pp. 528-534, vol. 46.

Heininger et al., The Effect of Human serum DNAases on the Ability to Detect Antibiotic-killed *Escherichia coli* in Blood by PCR. *J Med Microbial*, 2001, pp. 243-248, vol. 50.

Garg et al., Simple and Rapid Method for Extraction of DNA from Fresh and Cryopreserved Clotted Human Blood. *Clin Chem*, 1996, pp. 647-648, vol. 42.

Smith, Acyl-Enzymes as Thrombolytic Agents in a Rabbit Model of Venous Thrombosis. *Thromb Haemostas*, 1982, pp. 269-274, vol. 47.

Benjamin, *S. candida* Rugosa Lipases: Molecular Biology and Versatility in Biotechnology. *Yeast*, 1998, pp. 1069-1087, vol. 14.

Grotendorst, G.R., Purification and Partial Characterization of the Phospholipase A2 and Co-lytic Factor from Sea Anemone (*Aiptasia pallida*) Nematocyst Venom. *Toxicon*, 1999, pp. 1779-1796, vol. 37.

Kreilgaard, et al., Effects of Additives on the Stability of Recombinant Human Factor XIII During Freeze-drying and Storage in the Dried Solid. *Archiv Biochem Biophys*, 1998, pp. 121-134, vol. 360.

Diez et al., Isolation of Full-size mRNA from Cells Sorted by Flow Cytometry. *J Biochem Biophys Meth*, 1999, pp. 69-80, vol. 40.

Qiagen Qiamp blood mini kit handbook, 2003.

Von Pape et al., Platelet Function Analysis with PFA-100 in Patients Medicated with Acetylsalicylic Acid Strongly Depends on Concentration of Sodium Citrate Used for Anticoagulation of Blood Sample. *Thrombos Res*, 2000, pp. 295-299, vol. 98.

Sanyal, et al., An Effective Method of Completely Removing Contaminating Genomic DNA from an RNA Sample to be used for PCR. *Mol Biotechnol*, 1997, pp. 135-137, vol. 8.

Semple et al., Novel, Potent and Selective Chimeric FXa Inhibitors Featuring Hydrophobic P1-ketoamide Moieties. Bioorg Medicin Chern Lett, 2000, pp. 2305-2309, vol. 10.

Wang, et al., Polymyxin B binds to anaqndamide and inhibits its cylotoxic effect. *FEBS Lett*, 2000, pp. 151-155, vol. 470.

Wang et al., Simultaneous Measurement of Anandamide and 2-arachldonoylglycerol by Polymyxin B-Selective Adsorption and Subsequent HPLC . . . *Anal Biochem*, 2001, pp. 73-82, vol. 294.

Lee et al., Direct identification of *Vibrio vulnlficus* in Clinical Specimens by Nested PCR. *J Clin Microbiol*, 1998, pp. 2887-2892, vol. 36.

Zhang et al., Effect of Six Steroidal Saponins Isolated from *Anemarrhenae rhizoma* on Platelet Aggregation and Hemolysis in Human Blood. Clln Chlm Acta, 1999, pp. 79-88, vol. 289.

Pierre et al., Purification and Characterizaiton of the Cytochrome b6 f complex from *Chalmydomonas reinhardtii*. *J Bioi Chem*, 1995, pp. 29342-29349, vol. 270.

Watson K.C., Laboratory and Clinical Investigation of Recovery of *Salmonella typhi* from Blood. J elin Microbial, 1978, pp. 22-26, vol. 7, No. 2.

Zierdt et al., Development of a Lysis-filtration Blood Culture Technique. *J Clin Microbial*, 1977, pp. 46-50 vol. 5, No. 1.

Zierdt C.H. Blood-lysing solution nontoxic to pathogenic bacteria. J Clin Microbial, 1982, pp. 172-174, vol. 15, No. 1.

Kiss, C. et al. "Improved Subtractive Suppression Hybridization Combined with High Density cDNA Array Screening Identifies Differentially Expressed Viral and Cellular Genes" *Journal of Virological Methods*, Feb. 2003, pp. 195-203, vol. 107, No. 2.

Lönneborg, A. et al. "Reliable and Reproducible Method to Extract High Quality RNA from Plant Tissues Rich in Secondary Metabolites" *BioTechniques*, Oct. 2000, pp. 714-718, vol. 29, No. 4.

Park, Y. D. et. al. "Photopolymerized Hyaluronic Acid-Based Hydrogels and Interpenetrating Networks" *Biomaterials*, Mar. 2003, pp. 893-900, vol. 24, No. 6.

International Search Report for Application No. PCT/US2004/026606, 2004.

Fig. 3

*Bacillus anthracis* Blood Protocol Data Set

| Sample Number | pXO2 Primer / Probes - Crossing Point on Light Cycler | Genomic Primer / Probes - Crossing Point on Light Cycler | Ave. Calculated CFU/ 6 ml of blood | Comments on Sample Type All Samples Tested 2 Days Post Spiking |
|---|---|---|---|---|
| M3200253BA1 | 36.75 | 37.76 | 13.75 | Spiked Positive |
| M3200253BA2 | 36.59 | 37.86 | 13.75 | Spiked Positive |
| M3200253BA3 | 35.97 | 38.10 | 13.75 | Spiked Positive |
| M3200253BA4 | 37.26 | 39.53 | 13.75 | Spiked Positive |
| M3200253BA5 | 35.36 | 40.11 | 13.75 | Spiked Positive |
| M3200253BA6 | 36.35 | 45.19 | 13.75 | Spiked Positive |
| M3200253BA7 | 36.62 | 38.64 | 13.75 | Spiked Positive |
| M3200253BA8 | 37.04 | 39.51 | 13.75 | Spiked Positive |
| M320020BA9 | 0.00 | 0.00 | 0.00 | Blank |
| M/3200226BA1 | 37.16 | 39.35 | 1.38 | Spiked Positive |
| M/3200226BA2 | 36.79 | 40.28 | 1.38 | Spiked Positive |
| M/3200226BA3 | 37.92 | 39.94 | 1.38 | Spiked Positive |
| M/3200226BA4 | 37.49 | 40.16 | 1.38 | Spiked Positive |
| M/3200226BA5 | 39.66 | 40.26 | 1.38 | Spiked Positive |
| M/3200226BA6 | 39.31 | 41.19 | 1.38 | Spiked Positive |
| M/3200226BA7 | 38.48 | 40.73 | 1.38 | Spiked Positive |
| M/320020BA8 | 0.00 | 0.00 | 0.00 | Blank |

Fig. 4

*Bacillus anthracis* Blood Protocol Data Set: Comparison of Blood from Two Different Individuals and Evaluation of Blood Sample Age

| Sample Number | pXO2 Primer / Probes - Crossing Point on Light Cycler | Genomic Primer / Probes - Crossing Point on Light Cycler | Ave. Calculated CFU/ 6 ml of blood | Comments on Sample Type All Samples Extracted 84 Days Post Spiking |
|---|---|---|---|---|
| V210253BA1 | 37.73 | 39.81 | 10.5 | Blood Donor #1 |
| V210253BA2 | 36.74 | 39.05 | 10.5 | Blood Donor #1 |
| V210253BA3 | 36.51 | 37.99 | 10.5 | Blood Donor #1 |
| V210253BA4 | 38.12 | 39.79 | 10.5 | Blood Donor #1 |
| V21020BA5 | 0.00 | 0.00 | 0.00 | Blank |
| M210253BA1 | 37.86 | 39.81 | 2.25 | Blood Donor #2 |
| M210253BA2 | 37.84 | 39.22 | 2.25 | Blood Donor #2 |
| M210253BA3 | 37.24 | 38.52 | 2.25 | Blood Donor #2 |
| M210253BA4 | 38.68 | 39.33 | 2.25 | Blood Donor #2 |
| M21020BA5 | 0.00 | 0.00 | 0.00 | Blank |

Fig. 5

*Bacillus anthracis* Blood Protocol Data Set: Evaluation of Blood Protocol by a Department of Health Laboratorian

| Sample Number | pXO2 Primer / Probes - Crossing Point on Light Cycler | Genomic Primer / Probes - Crossing Point on Light Cycler | Ave. Calculated CFU/ 6 ml of blood | Comments on Sample Type: All Blood Samples Same Batch as in Table 1 |
|---|---|---|---|---|
| M3200256BA1L | 38.81 | 39.93 | 13.75 | Spiked Positive |
| M3200256BA2L | 36.10 | 39.26 | 13.75 | Spiked Positive |
| M/3200223BA3L | 36.77 | 38.58 | 1.38 | Spiked Positive |
| M320020BA4L | 0.00 | 0.00 | 0.00 | Blank |

Fig. 6

*Yersinia pestis* Blood Protocol Data Set

| Sample Number | YP 2 Primer / Probes - Crossing Point on Light Cycler | YP 9 Primer / Probes - Crossing Point on Light Cycler | YP12 Primer / Probes - Crossing Point on Light Cycler | YP 16 Primer / Probes - Crossing Point on Light Cycler | Ave. Calculated CFU/ 6 ml of blood | Comments on Sample Type All Samples Extracted 2 Days Post Spiking |
|---|---|---|---|---|---|---|
| M3180251EYP1 | 0.00 | 0.00 | 0.00 | 37.97 | 12.0 | Spiked Positive |
| M3180251EYP2 | 0.00 | 47.01 | 0.00 | 0.00 | 12.0 | Spiked Positive |
| M3180251EYP3 | 41.56 | 0.00 | 0.00 | 40.29 | 12.0 | Spiked Positive |
| M3180225EYP4 | 0.00 | 0.00 | 0.00 | 38.98 | 24.0 | Spiked Positive |
| M3180225EYP6 | 40.20 | 44.01 | 39.66 | 37.60 | 24.0 | Spiked Positive |
| M3180251FYP7 | 0.00 | 46.15 | 0.00 | 39.79 | 48.0 | Spiked Positive |
| M3180251FYP8 | 40.48 | 43.59 | 41.70 | 35.47 | 48.0 | Spiked Positive |
| M3180251FYP9 | 40.20 | 41.88 | 38.67 | 34.23 | 48.0 | Spiked Positive |
| M318020YP10 | 0.00 | 0.00 | 0.00 | 0.00 | 0.00 | Blank |

FIG. 17

Noise band crossing points for blood samples spiked with *B. anthracis* and processed with plasminogen, streptokinase, phospholipase $A_2$, DNase I, and lipase with centrifugation or filtration

| Amount *B. anthracis* Seeded (cfu) | Centrifugation Noise Band Crossing Points | | | Mean | Std. Dev. | Filtration Noise Band Crossing Points | | | Mean | Std. Dev. |
|---|---|---|---|---|---|---|---|---|---|---|
| ≤ 0.01 | | | | | | | | | | |
| ≤ 0.01 | | | | | | | | | | |
| ≤ 1.0 | | | | | | 40.33 | 39.89 | | 40.11 | |
| ≤ 1.0 | | | | | | | 37.79 | | 37.79 | |
| ≤ 2.0 | | | | | | 40.36 | | 37.69 | 39.03 | |
| ≤ 2.0 | 41.93 | | 40.31 | 41.12 | | | | | | |
| ≤ 5.0 | | | 40.47 | 40.47 | | 37.90 | 37.70 | 37.79 | 37.80 | 0.10 |
| ≤ 5.0 | 38.11 | | 40.36 | 39.24 | | 36.45 | 36.09 | 36.81 | 36.45 | 0.36 |
| ≤ 50.0 | 37.53 | 36.24 | 37.90 | 37.22 | 0.87 | 35.75 | 34.12 | 34.98 | 34.95 | 0.82 |
| ≤ 50.0 | 36.45 | 38.15 | 38.49 | 37.70 | 1.09 | 35.24 | 34.18 | 34.68 | 34.70 | 0.53 |

FIG. 18

Sedimentation and solublization of tissue aggregates from 6 ml blood samples exposed to various detergent and enzyme treatments

Enzyme treatments in a PBS/Triton X-100 buffer

|  | Triton X-100 in PBS | Pl.[c] 1U | Ph.[b] | Pl.[c] 1U Ph.[b] | Dn.[a] 1mg | Dn.[a] 1 mg Ph.[b] | Dn.[a] 1 mg Pl.[c] 1U Ph.[b] |
|---|---|---|---|---|---|---|---|
| % Observable pelleted tissue aggregate post centrifugation | 100 | 100 | 100 | 100 | 90 | 10 | 10 |
| Time (min) to solubilization of visible tissue aggregate in BLB[d] | > 360 | > 60 | > 60 | > 60 | < 10 | < 0.5 | < 0.5 |

[a] DNase I from the Roche MagNa Pure LC DNA Kit III
[b] Phospholipase $A_2$
[c] Plasminogen and 10K U streptokinase
[d] Bacterial Lysis Buffer from the Roche MagNa Pure LC DNA Kit III

FIG. 19

Filtration characteristics of 6 ml blood samples exposed to various detergent and enzyme treatments

Enzyme treatments in a PBS/Triton X-100 buffer

|  | Triton X-100 in PBS | Dn.[a] 1mg | Dn.[a] 1 mg Ph.[b] | Pl.[c] 5U | Pl.[c] 5U Dn.[a] 1mg Ph.[b] | Pl.[c] 5U Dn.[a] 0.2mg Ph.[b] | Pl.[c] 10U Dn.[a] 0.2mg Ph.[b] |
|---|---|---|---|---|---|---|---|
| Not filterable | + | + | + |  |  |  |  |
| Filterable with observable tissue aggregates |  |  |  | + |  | + |  |
| Filterable with out observable aggregates |  |  |  |  | + |  | + |

[a] DNase I from the Roche MagNa Pure LC DNA Kit III
[b] Phospholipase A$_2$
[c] Plasminogen converted to plasmin with 10K U streptokinase

EARLY DETECTION OF PATHOGENS IN BLOOD

CROSS REFERENCE TO RELATED APPLICATIONS

This application is a divisional of U.S. application Ser. No. 10/604,779, filed Aug. 15, 2003, which claims priority from U.S. Provisional Patent Application No. 60/319,474, filed Aug. 15, 2002 and U.S. Provisional Patent Application No. 60/319,803, filed Dec. 19, 2002, each of which is hereby incorporated by reference herein in its entirety, including any figures, tables, nucleic acid sequences, amino acid sequences, and drawings.

FEDERAL RESEARCH STATEMENT

The present invention was made with the support of the U.S. Army Soldier and Biological Chemical Command under Grant No. DAAD13-01-C-0043. The Government has certain rights to this invention. Research and validation of the present invention was conducted at the Center for Biological Defense at the University of South Florida. The mission of the Center is to identify and develop new and innovative methods for recognizing and combating terrorism, and to promote the establishment of a bioterrorism preparedness program.

BACKGROUND OF INVENTION

This invention relates to a method of detecting blood infections at an early stage of infection and more particularly to a method of detecting pathogens at low concentrations in circulation from a volume of blood.

The threat of bioterrorism (BT) and biological warfare presents challenges for the clinical setting that are best met with rapid and sensitive technologies to detect BT agents. Peripheral blood samples could contribute to early and specific clinical and epidemiological management of a biological attack if detection could take place when the concentration of the infecting organism is still very low. The worried well and recently infected patients would benefit, both psychologically and physically, from early pharmacological intervention.

Infection with *Bacillus anthracis* or *Yersinia pestis* often present initially as a nonspecific febrile or flu-like illness. The mediastinitis associated with inhalational anthrax ultimately results in bacilli entering the blood once the efferent lymphatics become laden with organisms. When bacteremia (the presence of bacteria in the blood) and sepsis (the invasion of bodily tissue by pathogenic bacteria) have initiated, the number of bacilli may increase quickly, doubling every 48 minutes, most often resulting in death of the patient.

It has been reported that microbiological studies on patient blood samples are useful for diagnosing pneumonic plague. The potential for *Yersinia pestis* bacilli to be present in peripheral circulating blood suggests that a PCR assay would make a useful diagnostic tool. Testing for pneumonic plague or inhalational anthrax would be effective when healthy patients present with "flu-like" symptoms (malaise, fever, cough, chest pain and shortness of breath) that may accompany other nonspecific symptoms. However, in order to maximize the probability of successful, detection of the infecting organism must take place early in the disease process, when the concentration of circulating bacteria is very low.

Extraction of pathogen DNA from whole blood typically requires between 200 µl to 500 µl of patient sample for each preparation event. Detection of early bacteremia is improved by using an entire 6 ml tube of patient blood for a single sample preparation event. Prior art literature describes a single tube blood culture system exploiting the selective lysis of blood elements, followed by centrifugation to pellet bacteria for plating on solid media. The technique has been examined thoroughly in conjunction with microbiological testing.

Accordingly, what is needed in the art is: 1) a method of destroying and making soluble the spectrum of blood element components (erythrocytes, leukocytes, nuclear membranes, fibrin, and host nucleic acid) without damaging analyte particles (bacteria, virus, fungi, toxin, metabolic markers, disease state markers, or chemical agents) in order to expose and rapidly concentrate (via centrifugation, filtration, or capture) the analyte particles from large volumes of blood, 2) removal of the host DNA and the matrix associated biomass present in the large volume blood sample using a single step enzyme detergent cocktail that is amenable to automation and portable systems, and 3) an analyte particle concentration method that can be coupled to existing manual or automated processes for nucleic acid extraction, biosensor testing, or liquid chromatography separation and mass spectrometry analysis.

It is, therefore, to the effective resolution of the aforementioned problems and shortcomings of the prior art that the present invention is directed.

However, in view of the prior art in at the time the present invention was made, it was not obvious to those of ordinary skill in the pertinent art how the identified needs could be fulfilled.

SUMMARY OF INVENTION

Fibrin is an insoluble protein precipitated from blood that forms a network of fibers. In vivo, this process is central to blood clotting. Fibrin is created by the proteolytic cleavage of terminal peptides in fibrinogen. In the laboratory analysis of blood, an aggregate (pellet) of fibrin collects at the bottom of a tube when blood is centrifuged. Within the fibrin aggregate, pathogens are trapped. The analysis of these pathogens is highly desirable. However, like coins embedded in a slab of concrete, the captured pathogens are substantially hidden from analysis, trapped in the fibrin aggregate. For individuals potentially exposed to dangerous pathogens, time is of the essence and rapid identification of the captured pathogens is paramount.

Plasmin is a substance in blood capable of converting fibrin to fibrinogen monomers. Plasminogen is a precursor of plasmin in the blood. Streptokinase is an enzyme that activates plasminogen to form plasmin. The combination of plasminogen and streptokinase in the presence of the fibrin aggregate containing blood elements and bacteria (formally present in peripheral circulation) allows the conversion of the fibrin aggregate to a liquid state.

This conversion facilitates rapid and efficient pathogen analysis through blood culture, antibody based testing, or nucleic acid sequence based testing (Reverse Transcription PCR, PCR, NASBA, TMA or the like).

The addition of DNAse (a DNA nuclease) to the above-described reaction provides for the conversion of human DNA into short fragments. This conversion of human DNA into short fragments contributes to a more rapid and efficient protein hydrolysis process during DNA extraction. This conversion of human DNA into short fragments is done while the bacterial DNA is protected. The short fragment human DNA is carried less efficiently through the DNA extraction process and hence represents a smaller proportion of total DNA product. As a result, the reduced human DNA level presents less of an inhibitory component to the nucleic acid sequence based reactions.

The present invention is a method of extracting infectious pathogens from a volume of blood including the steps of creating a fibrin aggregate confining the pathogens and introducing a fibrin lysis reagent to expose the pathogens for analysis and DNAse to facilitate DNA extraction. The fibrin lysis reagents may be composed of DNAse, plasminogen and streptokinase frozen in coincident relation until the fibrin lysis reagent is needed whereby streptokinase enzymatically reacts with plasminogen to form plasmin upon thawing and introduction into the fibrin sample. Preferably, the plasminogen is suspended in an aqueous salt solution prior to freezing including NaCl and $Na_3PO_4$. The fibrin lysis reagent is preferably composed of DNAse and Phospholipase $A_2$. The DNAse enzyme is used to facilitate the chemical and physical disruption of pelleted blood elements that result from the previously described protocol. Phospholipase $A_2$ is used to help human DNA digestion by destroying phospholipid bilayers and, hence, destruction of the nuclear membrane.

The present invention utilizes resuspension of the dried enzymes in a buffer solution using Potassium Phosphate as an aide to blood element solublization. It is imperative that the streptokinase and plasminogen are not mixed with the buffer solution until immediately prior to the addition of the blood sample. The Potassium Phosphate pH range is 7.8 to 8.0, differentiated from prior art claiming an effective pH range of 7.2 to 7.6. Prior art uses phosphate ion solutions with lower pH to act as a true buffer, however, the current method allows for optimal Phospholipase $A_2$ activity and Magnesium solubility. Magnesium is found in the buffer solution as the divalent cation driving the activity of Phospholipase $A_2$ in the presence of DNAse. Prior art uses calcium as the classic divalent cation for driving Phospholipase $A_2$ activity, however, calcium is not compatible with the phosphate ions essential for blood element solublization.

An embodiment of the present invention includes concentrating and extracting particles such as prions, toxins, metabolic markers, cancerous matter, disease state markers, bacteria, virus, and fungi from a volume of blood by introducing an enzyme-detergent combination to expose pathogens in the blood sample and analyzing the blood sample for the particles now readily identifiable via the extraction. The enzyme-detergent may be a fibrin lysis reagent comprising plasminogen and streptokinase. The plasminogen and streptokinase may be frozen in coincident relation until the fibrin lysis reagent is needed. The streptokinase then reacts with the plasminogen to form plasmin upon thawing. The plasminogen may be suspended in an aqueous salt solution prior to freezing. Suitable salt solutions may include NaCl, $NaPO_4$ or the like. To enhance analysis, the particles may be replicated via polymerase chain reactions (PCR).

By introducing DNase, the process is facilitated by the conversion of DNA into short fragments thereby contributing to a more rapid and efficient protein hydrolysis process during DNA extraction and lowering the burden of inhibitory human DNA. Similarly, introduction of Endonuclease produces a similar advantage.

As an alternative to freezing, the enzyme-detergent may include dried streptokinase and dried plasminogen as the fibrin lysis reagents. The dried reagents may then be mixed and distributed into disposable test containers. This embodiment may be particularly useful for field-testing in locations where sophisticated laboratory equipment and controls are unavailable.

The plasminogen may be combined with Phospholipase A2. DNase, Endonuclease, Lipase, and combinations thereof. The dried enzyme-detergent combination may be suspended in pellets of trehalose buffer and packaged into tubes as a dry reagent. The dried reagents may then be resuspended in a buffer, added to a 1-10 ml volume of blood and incubated for 5-20 minutes at room temperature. More specifically, the dried reagent is comprised of 1,500-4,500 KU Phospholipase A2, 5,000-10,000 U Streptokinase, 2-10 U Plasminogen, 200-3,650 U DNase, 200-4,000 U Endonuclease, and 10,000-100,000 Lipase.

The solution may be centrifuged for approximately 20 minutes at 5,000-5,500×g at a temperature of 10-20° C., the supernatant decanted, and the pellet washed. The pellet may be washed three times with a 10-20 mM solution of Ecotine/20 mM HEPES pH 7.7 and/or a 10-20 mM solution of sucrose/20 mM HEPES pH 7.7. The resultant sample may then be applied to a commercially available nucleic acid extraction method.

Digesting the sample may include lysis and DNase inactivation or lysis and Endonuclease inactivation. 12.5-25 mg proteinase K, 1-105% SDS (sodium dodecyl sulfate), 10-200 mM aurintricarboxylic acid, and 10-20 mM sodium citrate buffer pH 7.8-8.4 may be utilized, the solution allowed to incubate at room temperature for 10 minutes. The sample may then be filtered with a 0.22-0.45 µm filter unit, washed with 10-200 mM Aurintricarboxylic Acid, digested with lysis and DNase inactivation and/or Endonuclease inactivation, and purified.

Digesting the sample may include the steps of combining 12.5-25 mg proteinase K, 1-1.5% SDS, 10-200 mM aurintricarboxylic acid, and 10-20 mM sodium citrate buffer, incubating at room temperature for 10 minutes, and eluting the lysate from the filter surface by addition of 3.5-4.2 M guanidine isothiocyanate pH 6.4.

The solutions may be applied directly to a biosensor device wherein, responsive to the presence of the pathogens in the blood sample, the patient develops pathogenic or native disease state markers that allow for the capture and detection of these markers by the biosensor device. Alternatively, the solution may be applied directly to a liquid chromatography mass spectrometry device whereby, responsive to the presence of the pathogens in the blood sample, the patient develops pathogenic or native disease state markers that allow for the detection of mass signatures associated with the structural components of the pathogens using the mass spectrometry device.

The buffer may contribute detergent and salts. This may be achieved by aiding blood element solublization by introducing 10-30 mM Potassium Phosphate at a pH range of 7.8 to 8.0, driving Phospholipase $A_2$ activity by adding 10-80 mM Magnesium Chloride as the divalent cation, adding 20-150 mM Sodium Chloride, and including 10-200 mM Aurintricarboxylic Acid during the DNase incubation process. The buffer may also include 1.0-1.2% TRITON X-100 (octylphenol ethoxylate). Additional steps may include combining 20-35 mM methyl 6-O-(N-heptylcarbamoyl)-α-D-glucopyranoside and 0.05-0.1% Saponin; and storing the enzymes by using a trehalose buffer. Storing the enzymes is accomplished by using a trehalose buffer in combination with methyl 6-O-(N-heptylcarbamoyl)-α-D-glucopyranoside. The trehalose storage buffer comprises 10 mM Potassium Phosphate, 0.01-0.04% TRITON X-100 (octylphenol ethoxylate), 1-5 mM Dithiothreitol, and 0.3-0.5 M Trehalose.

BRIEF DESCRIPTION OF DRAWINGS

For a fuller understanding of the nature and objects of the invention, reference should be made to the following detailed description, taken in connection with the accompanying drawings, in which:

FIG. 3 is a table providing data on *Bacillus anthracis* blood protocol.

FIG. 4 is a table providing data on a comparison of two blood samples from different individuals.

FIG. 5 is a table providing data on an evaluation of the present method by a Department of Health laboratorian.

FIG. 6 is a table providing data on *Yersinia pestis* blood protocol.

FIG. 17 is a table providing data on noise band crossing points for blood samples spiked with *B. anthracis* and processed with plasminogen, streptokinase, phospholipase $A_2$, DNase I, and lipase with centrifugation or filtration.

FIG. 18 Sedimentation and solublization of tissue aggregates from 6 ml blood samples exposed to various detergent and enzyme treatments.

FIG. 19 Filtration characteristics of 6 ml blood samples exposed to various detergent and enzyme treatments.

DETAILED DESCRIPTION

Figure 1:
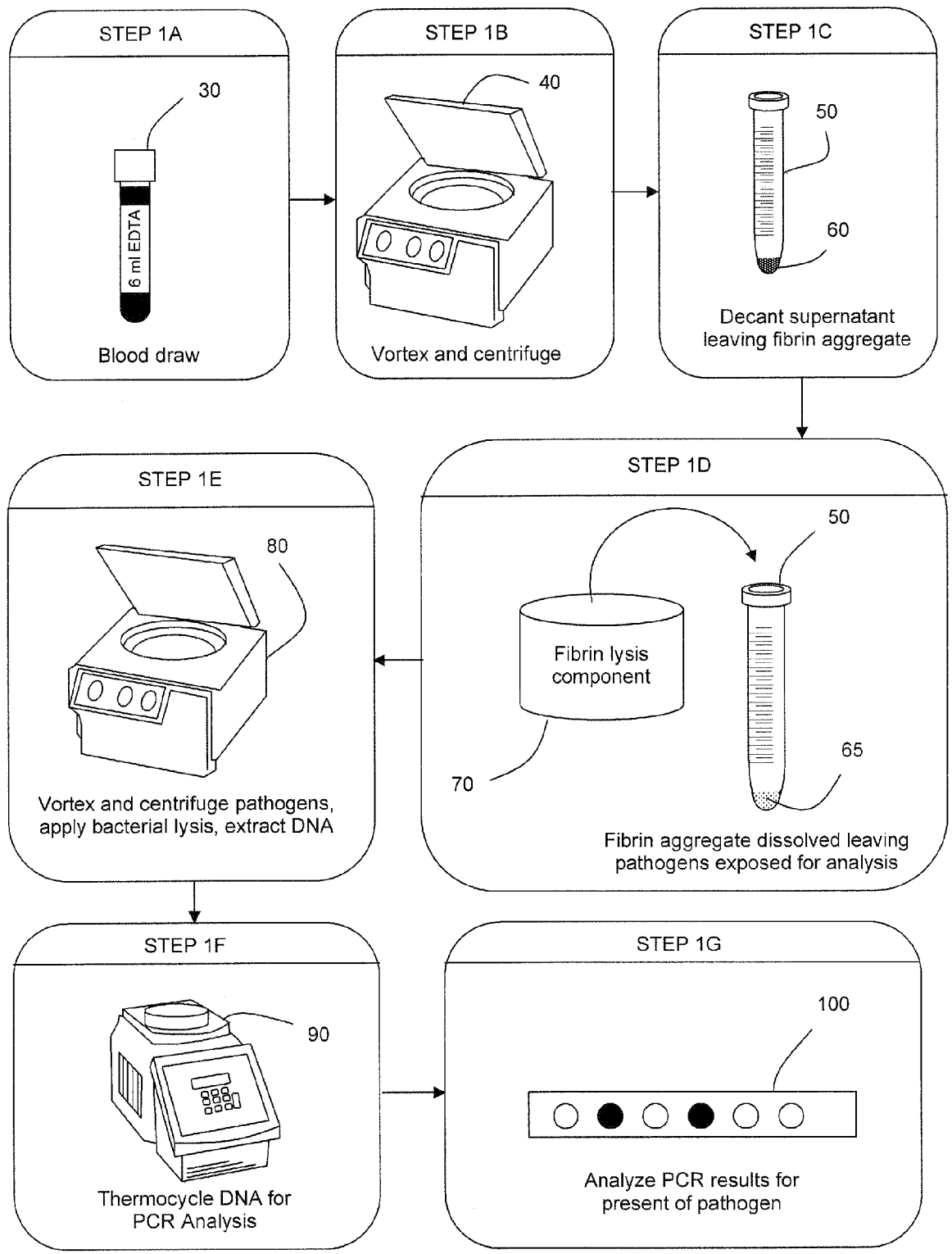
FIG. 1 is a diagrammatic view of the method according to the invention according to the invention.

In FIG. 1, a blood draw 30 is performed on a patient. A solution of PBS, pH 7.4 and 1.2% TRITON X-100 is added, the blood is vortexed and centrifuged 40 creating pellet 60 in a 15 ml tube 50. Preferably, resins, metal hydroxides, and/or nano materials may be added with the PBS/TRITON X-100 solution to capture particles such as bacteria, virus, fungi, cancerous cells, prions, toxins and the like to contribute greater density to these particles. The increase in particle density allows lower speeds to run during centrifugation.

The supernatant is decanted leaving a fibrin aggregate. A fibrin lysis component 70 is added to tube 50 dissolving the fibrin aggregate and leaving pathogens 65 exposed for analysis. Pathogens 65 are vortexed, centrifuged, and subject to lysis to extract the pathogen DNA. The DNA is then replicated 90 and analyzed 100 for the identity of the suspected pathogen.

In an alternative embodiment of the invention, a device would be used to obviate the need for a centrifuge. The device will use flexible electrodes similar to a fish gill to collect particles (such as bacteria, virus, cancerous cells, prions, or toxins). The electrodes will also be used to collect resins and nano materials that have these particles attached to them. The device will resemble a bubble on a surface. An electrical potential will be used to accelerate pathogen capture. The device can be compressed to allow efficient removal of the contents. The device would preferably have the following properties: (1) a rigid base layer and flexible top layer; (2) flexible gills to be mounted on either the top or bottom layer; (3) Strepavidin and hyaluronic acid strands functionalized with bioactive peptides, antibodies, aptomers, molecular imprinted polymers, or metals that attract particles such as bacteria, virus, fungi, toxins, metabolic markers, disease state markers, or chemical agents are to be deposited on the flexible gill electrodes; (4) the flexible layer will have electrodes deposited on it; (5) counter electrodes for the gill electrodes will reside on the opposite side; (6) the average dead volume of the device is 300 micro liters it is preferred that there is to be no residual material in the device after squeezing out the material from the device; and (7) polyimide will form the flexible portion and the electrodes will be made of Pt, Au, or carbon. The device is preferably used as follows: (1) flow liquid into the device and apply voltage at this time; (2) add chemicals and heat the device; and (3) squeeze out the device to remove all contents. The device is used to prepare a sample for analysis of particles (such as bacteria, virus, cancerous cells, prions, or toxins) using spectrophotometric, mass spectroscopy, antibodies, culture, or nucleic acid (e.g. PCR, NASBA, TMA) based detection systems.

A filtering device may be used to filter out the particles from blood treated with the TRITON X-100/PBS/magnesium solutions with enzymes selected from the group of streptokinase, plasminogen, phospholipase $A_2$, DNase, and lipase. A filtering device may also be used to filter out the particles from blood treated with a combination of methyl 6-O-(N-heptylcarbamoyl)-α-glucopyranoside, Saponin, and PBS/magnesium plus enzymes selected from the group of streptokinase, plasminogen, phospholipase $A_2$, DNase, and lipase. After washing away the enzyme and detergent treatment reagents and any residual broken down blood components, the particle is ready for analysis or further processing.

Figure 2:
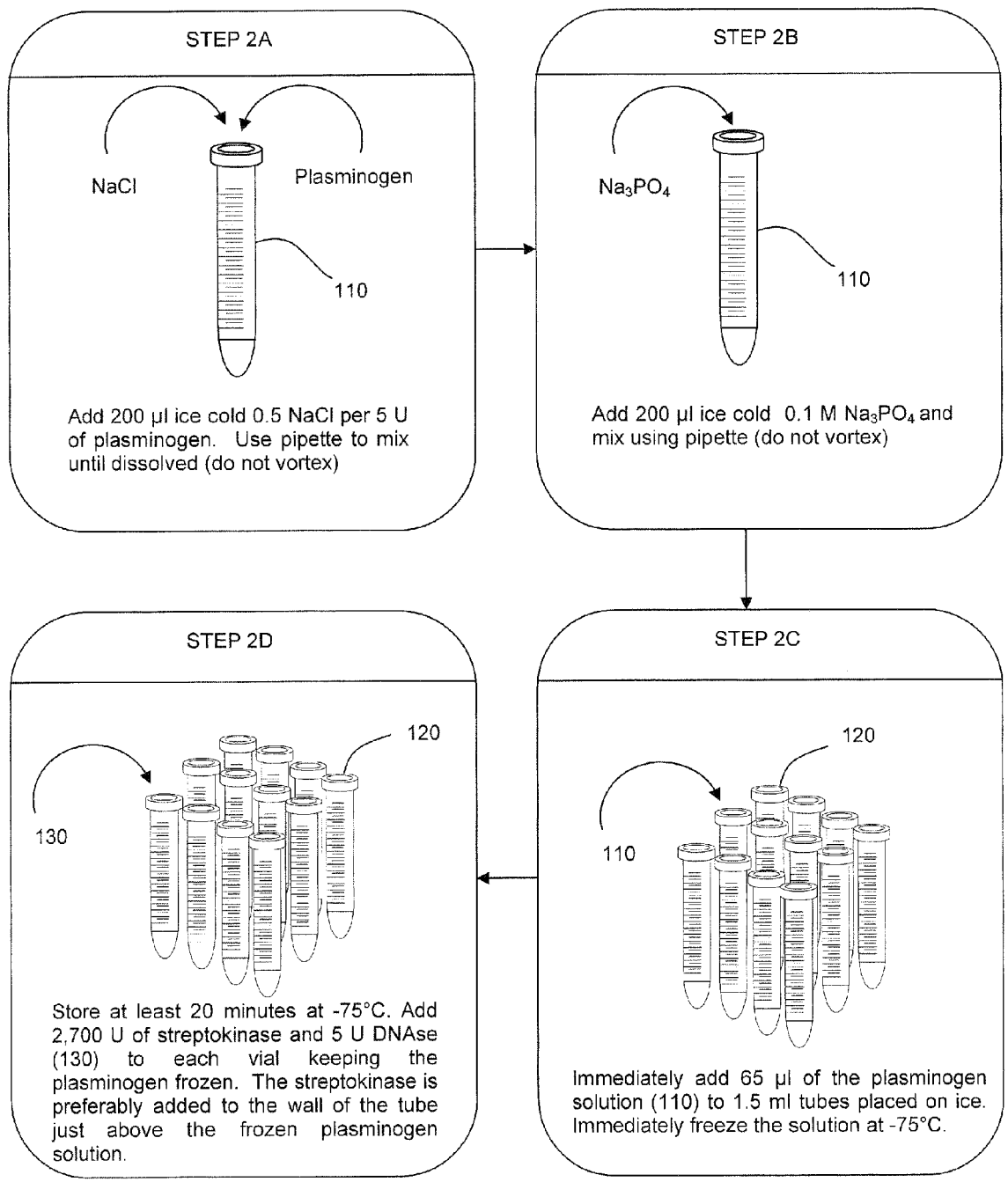
FIG. 2 is a diagrammatic view of the preparation of the fibrin lysis reagent according to Protocol 1 of the invention.

The preparation of the fibrin lysis reagent is shown as Protocol 1 in FIG. 2 wherein NaCl, MnCl, DTT, DNAse, and plasminogen are added to mixing tube 110. Sodium phosphate is then added to mixing tube 110 and the solution is distributed into 1.5 ml reagent tubes 120 placed on ice. The reagent tubes 120 are frozen to −75° C. for approximately 20 minutes. Approximately 2,700 U of streptokinase 130 is added to the wall of reagent tubes 120 just above the frozen plasminogen solution.

FIGS. 3-6 provide PCR results derived from testing blood samples seeded with encapsulated vegetative avirulent *Bacillus anthracis* were grown according to CDC protocol # CDC.DFA.1.2, stored in 15% glycerol TSB, and frozen at −75° C. Stocks of avirulent *Yersinia pestis* grown in TSB at 37° C., frozen in 15% glycerol TSB, and frozen at −75° C. Bacterial counts were tested at the time of harvest and retested at the time of sample spike.

Figures for average *Bacillus anthracis* CFU per six ml of human blood are derived from post-freezing testing given the large standard deviation encountered in side-by-side post freezing dilution events. No significant cellular death is recognized or expected. A 30% cellular death rate is the highest that is reasonably expected in the worst circumstances. A conservative approach would be to increase all calculated *Bacillus anthracis* CFU by 30%.

Figures for average *Yersinia pestis* CFU per six ml of blood are derived from pre-freezing testing. The low standard deviation of pre-freezing count replicates and concordance with post-freezing testing allows use of the pre-freezing bacteria count numbers. This is a conservative approach that can be utilized given the now predictable results that are derived from storing and diluting this organism.

The present invention reproducibly generates analyte DNA appropriate for PCR testing of *Bacillus anthracis* using patient blood samples that are up to 3 months old Sensitivity is 100% at <10 CFU/ml of human blood when using 6 ml of blood collected in a Becton Dickinson Vacutainer (Tables 1 and 2). This protocol also allows detection of *Yersinia pestis* at 100% sensitivity at <10 CFU/ml for at least one of four oligo sets according to the more limited data gathered for this organism (Table 3). It should be noted that CDC does not consider samples positive for *Y. pestis* unless two oligo sets produce an acceptable PCR signal.

Figure 7:
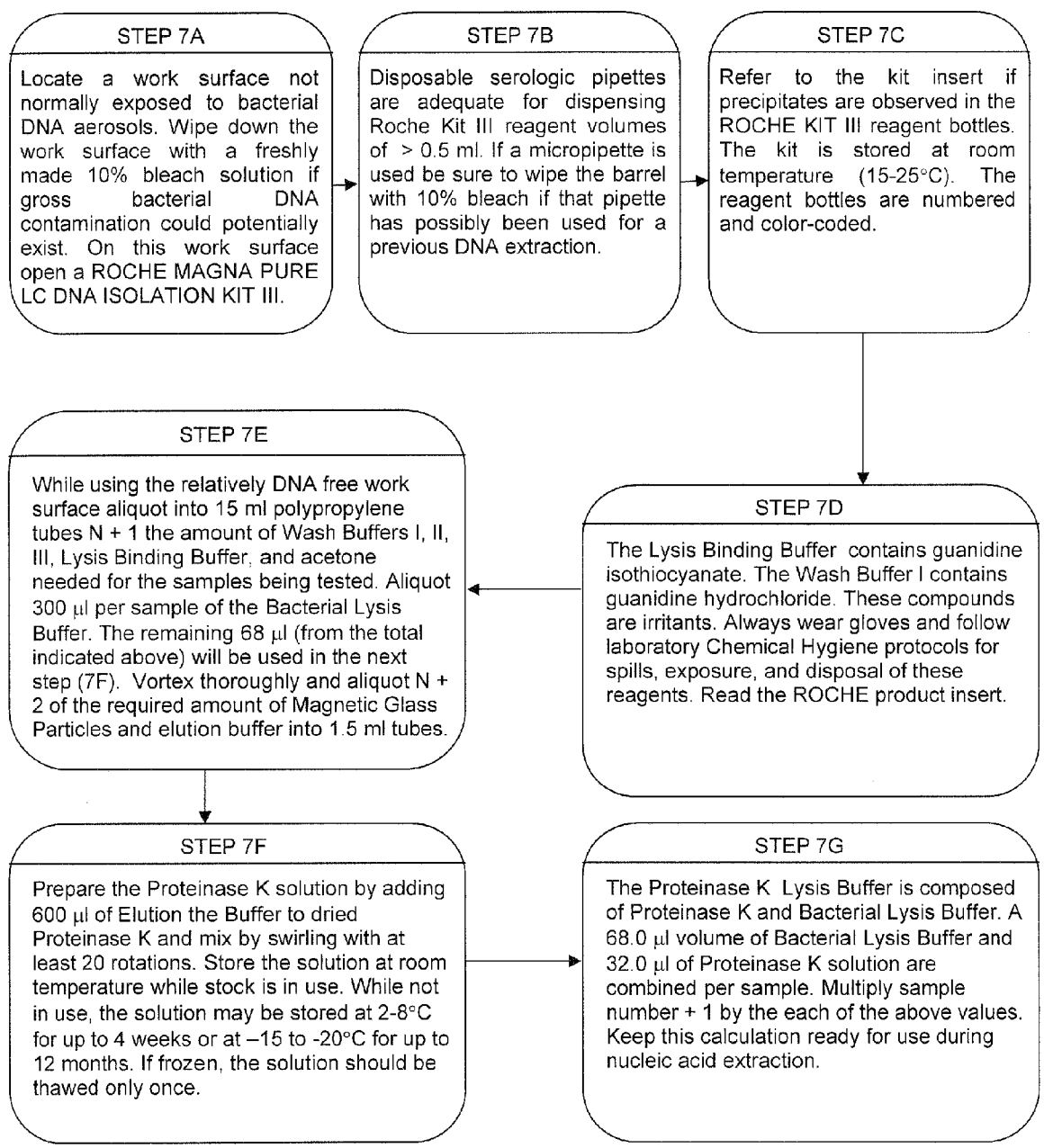
FIG. 7 is a diagrammatic view of the setup of extraction reagents according to Protocol 1 of the invention.
Figure 8:
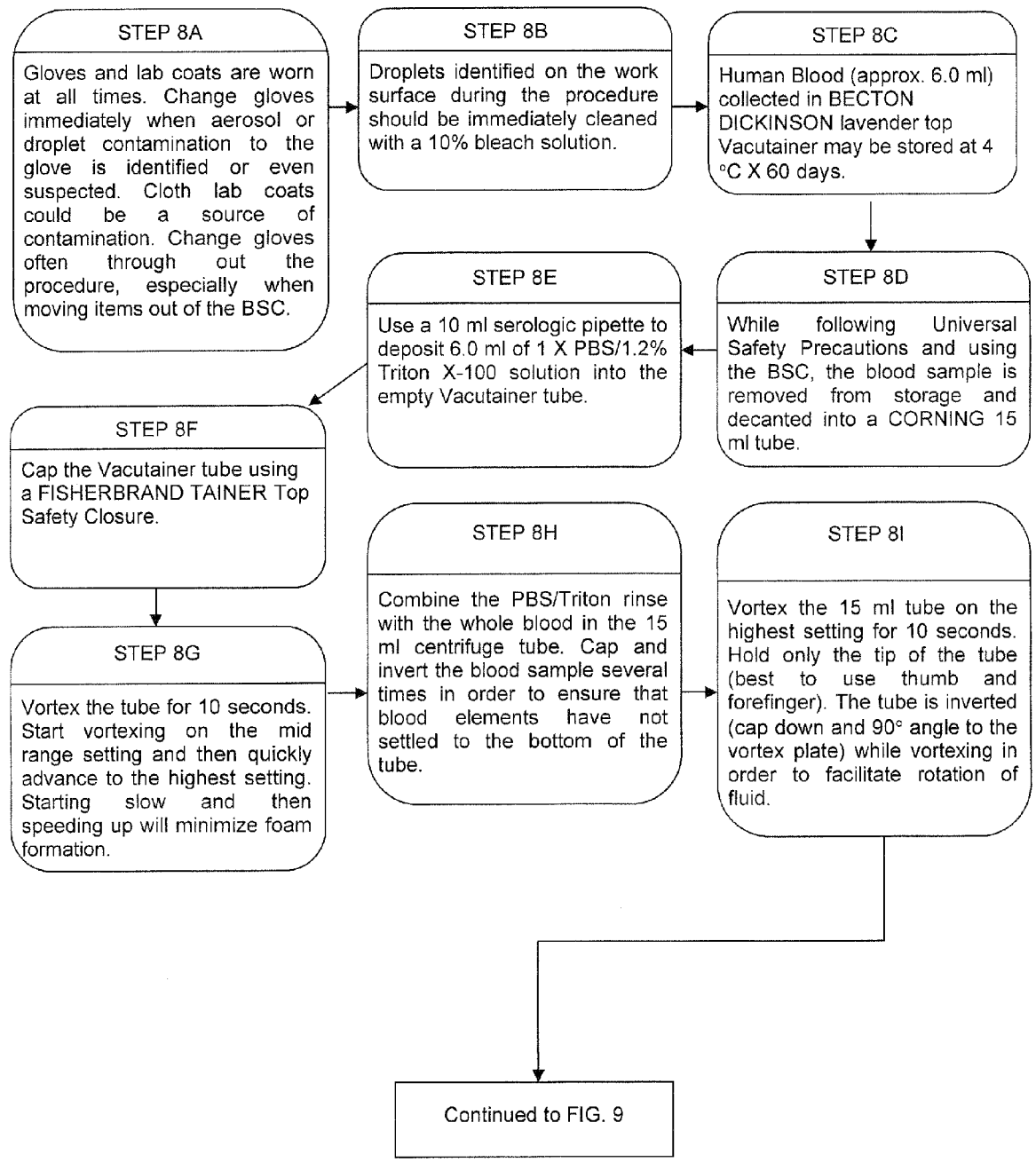
FIGS. 8-9 are diagrammatic views of bacterial recovery and fibrin lysis according to Protocol 1 of the invention.
Figure 9:
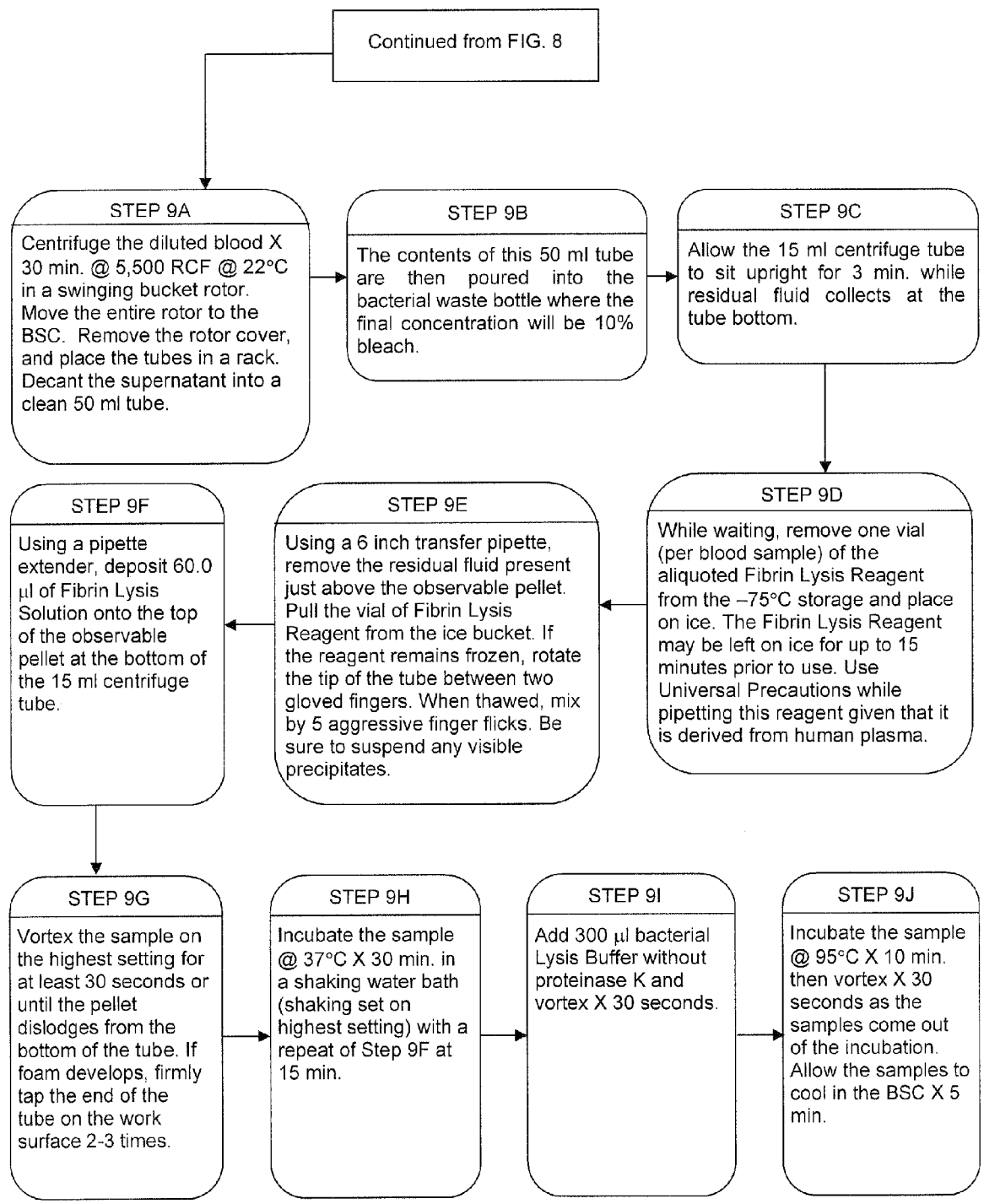
Figure 10:
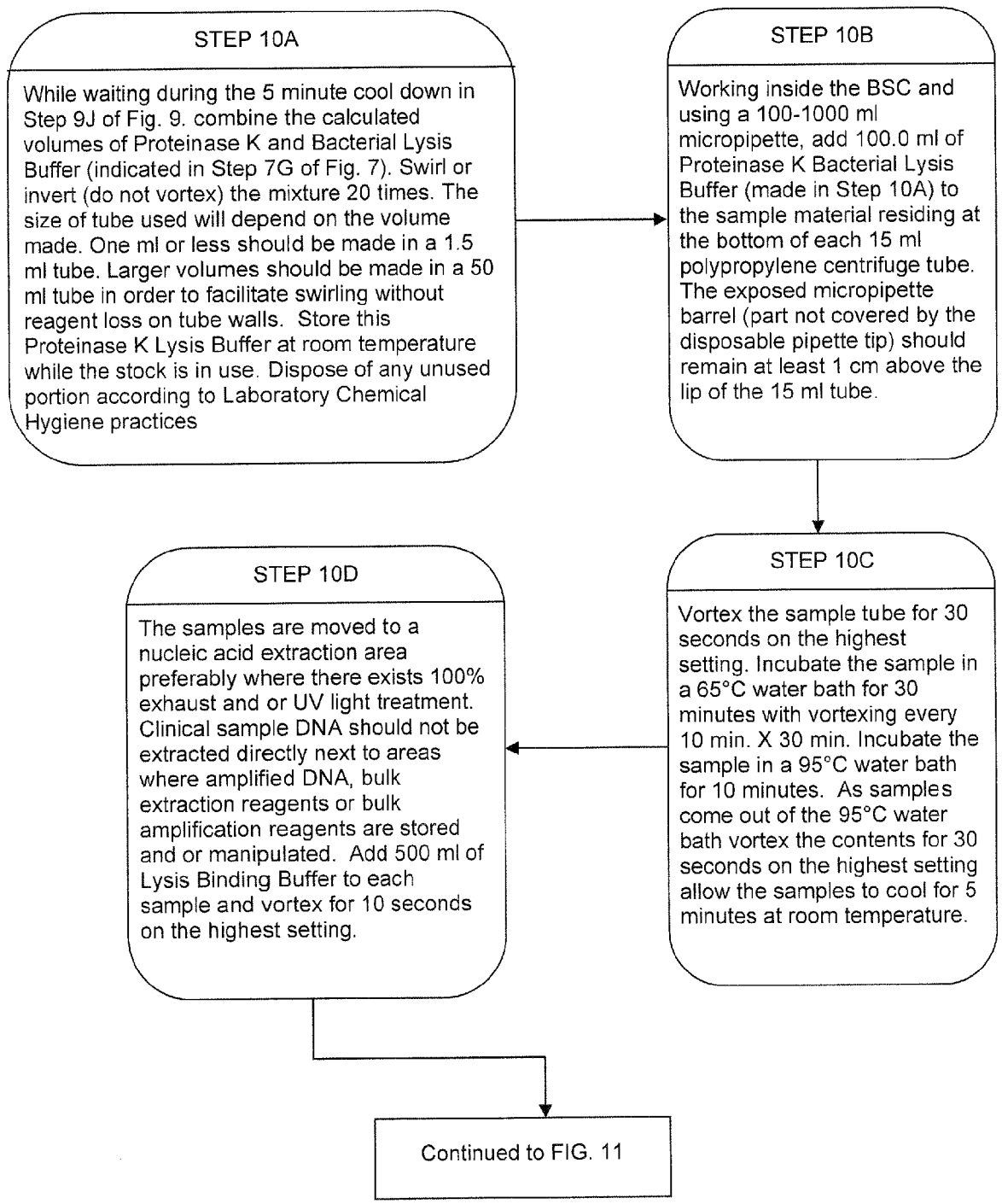
FIGS. 10-13 are diagrammatic views of bacterial lysis and nucleic acid extraction according to Protocol 1 of the invention.
Figure 11:
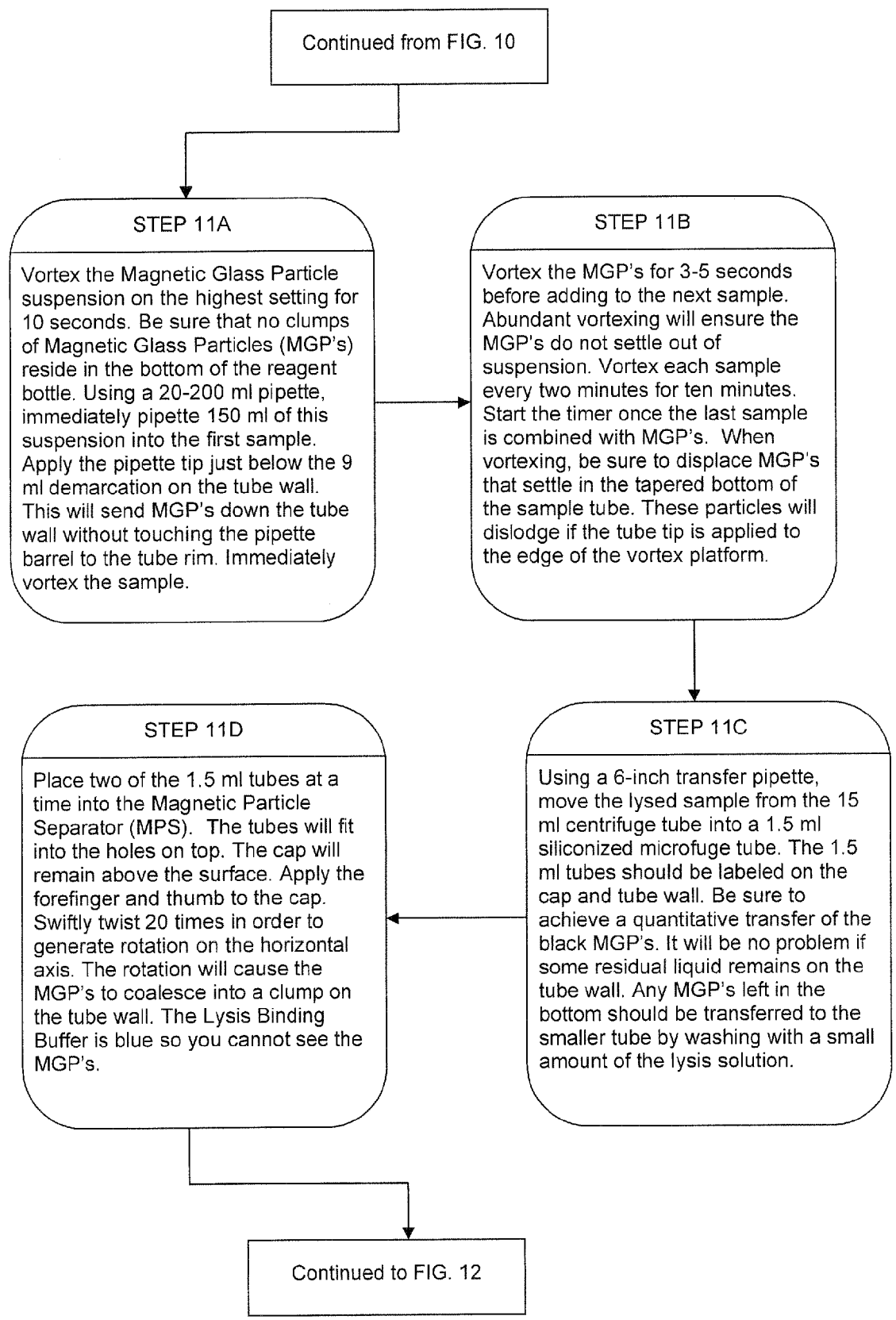
Figure 12:
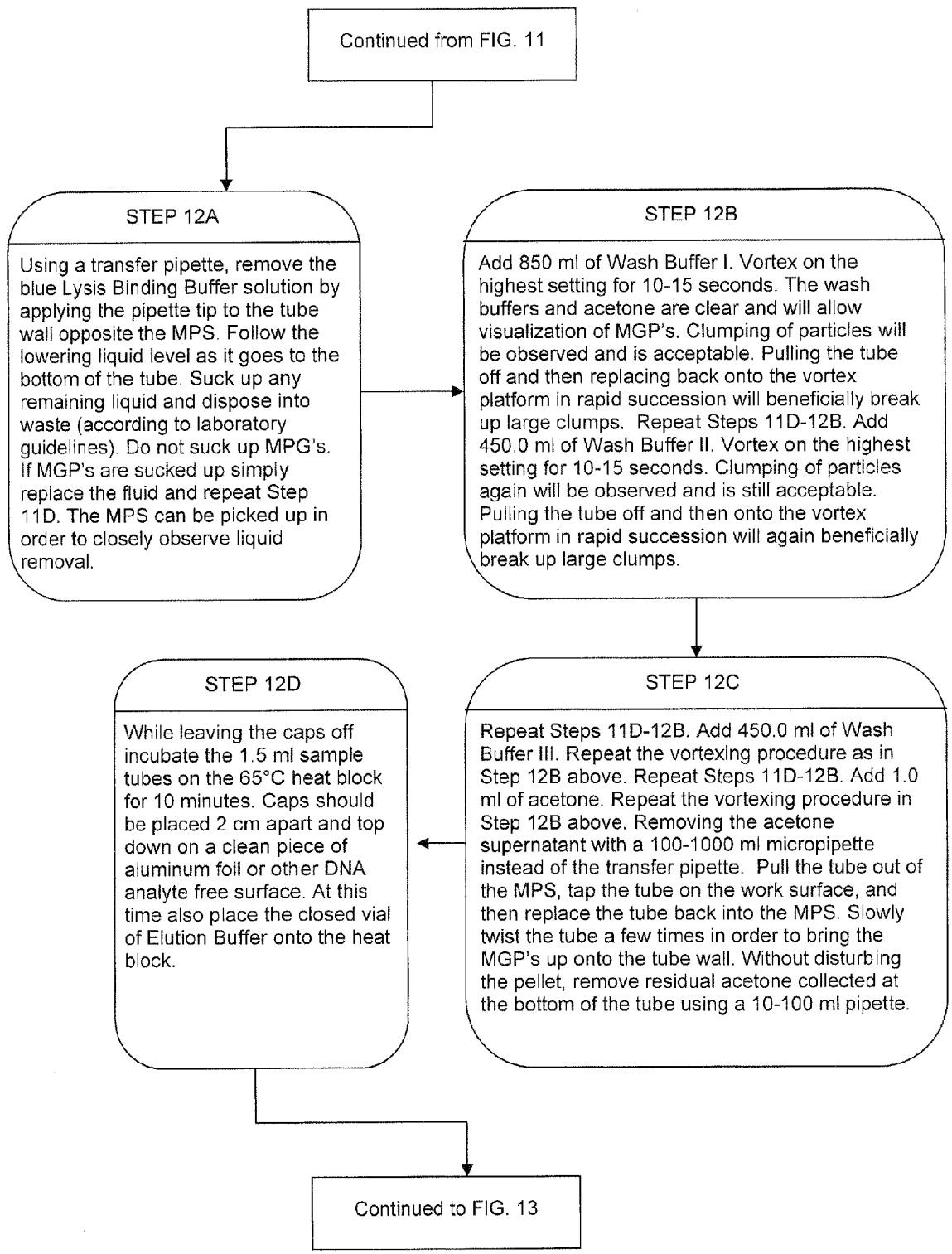
Figure 13:
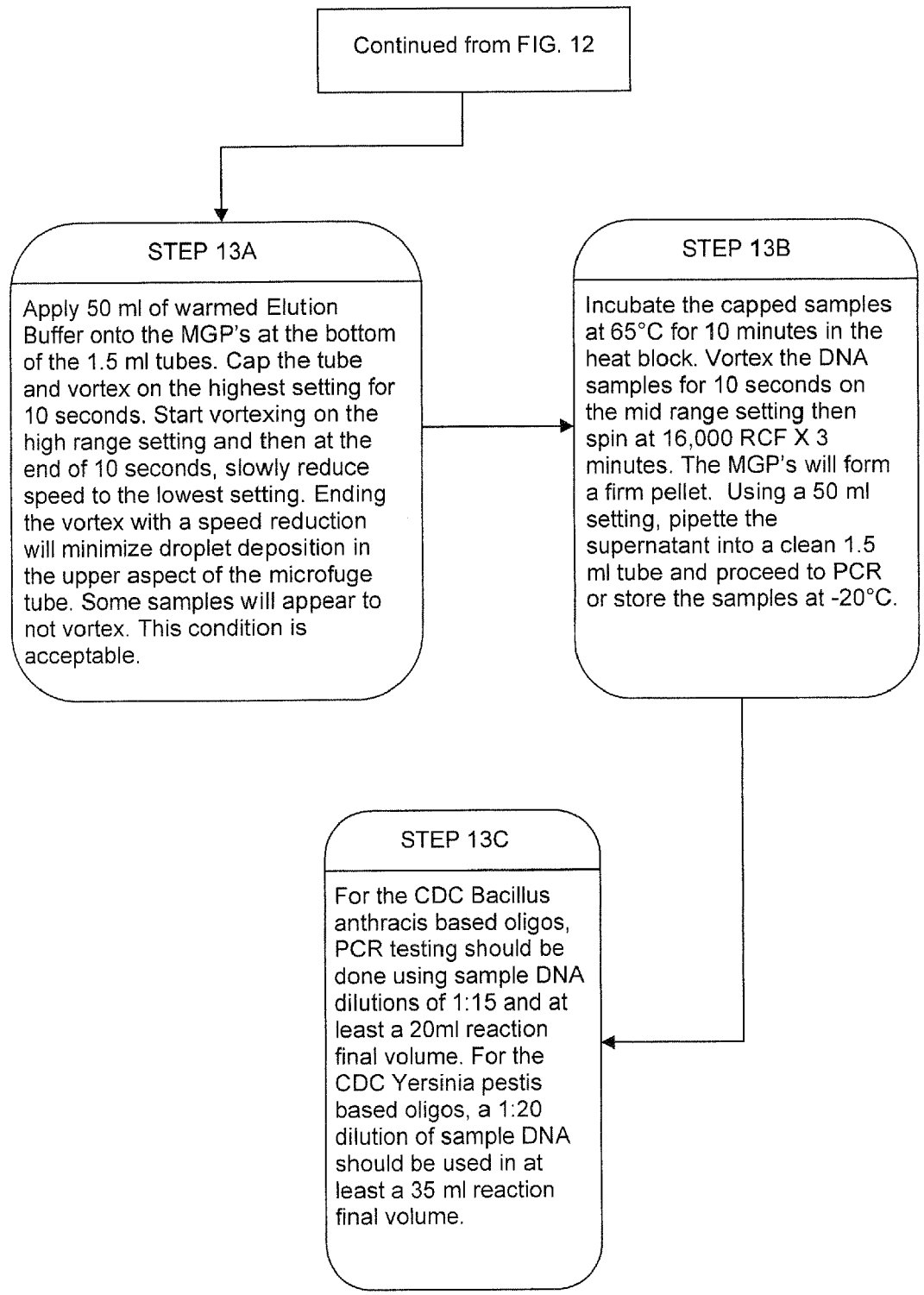

In accordance with Protocol 1, FIG. 7 shows a method of the setup of extraction reagents according to the invention. FIGS. 8-9 show a method of bacterial recovery and fibrin lysis according to the invention. FIGS. 10-13 show a method of bacterial lysis and nucleic acid extraction according to the invention.

In an alternative embodiment, as shown in FIGS. 14-16b, the individual enzymes of streptokinase and plasminogen are made into dried powders, mixed, then distributed to disposable tubes. Alternatively, Phospholipase $A_2$, plasminogen, DNase or Endonuclease, and lipase are suspended and dried in pellets of trehalose buffer. Phospholipase $A_2$ or any enzyme that will destroy nuclear membrane while keeping bacterial cell wall or viral coats in tact may also be used. Streptokinase is likewise suspended and dried in pellets of trehalose buffer. At least one pellet of the plasminogen and one pellet of the streptokinase are packaged into tubes as dried reagents.

The dried reagents previously described are then resuspended in a 10 ml buffer solution comprising 10-30 mM Potassium Phosphate, 10-80 mM Magnesium Chloride, 20-150 mM Sodium Chloride, 10-200 mM Aurintricarboxylic Acid and 1.0-1.2% TRITON X-100. Aurintricarboxylic Acid is evidenced to provide a level of protection to bacterial nucleic acid without impeding human DNA digestion. The use of Aurintricarboxylic Acid is not found in prior methods of human DNA digestion. Exclusion of TRITON X-100 is permitted upon addition of 20-35 mM methyl 6-O-(N-heptylcarbamoyl)-α-D-glucopyranoside and 0.05-0.1% Saponin. The methyl 6-O-(N-heptylcarbamoyl)-α-D-glucopyranoside is stored with the phospholipase $A_2$, plasminogen, DNase I, and lipase in a Trehalose storage buffer. Substitution of the TRITON X-100 with the methyl 6-O-(N-heptylcarbamoyl)-α-D-glucopyranoside and saponin solution allows for the efficient activity of Phospholipase $A_2$, provides the action of breaking up protein aggregates without denaturation, and is more genial to bacterial walls than TRITON X-100. Use of Saponin and methyl 6-O-(N-heptylcarbamoyl)-α-D-glucopyranoside in this combination is lacking in prior art. The Trehalose storage buffer comprises of 10 mM Potassium Phosphate pH 7.4, 0.01-0.04% TRITON X-100 or methyl 6-O-(N-heptylcarbamoyl)-α-D-glucopyranoside, 1-5 mM Dithiothreitol, and 0.3-0.5 Trehalose. The buffer and enzyme mix are then immediately combined with a 10 ml blood sample, which may be scaled down to 1 ml. The sample is then incubated at room temperature for 5-10 minutes. The aforementioned components aide blood element solubilization through minimizing certain particulates that would otherwise clog filters, impair biosensors or mass spectrometry devices, and impede nucleic acid extraction. Solublization occurs while human DNA is efficiently digested and as viral and/or bacterial DNA remain intact.

In accordance with Protocol 2 and 4, the enzyme combination is comprised of Streptokinase, Plasminogen, DNase or Endonuclease, Phospholipase $A_2$, and Lipase. Alternatively, enzyme combinations comprising of Streptokinase, Plasminogen, DNase or Endonuclease, and Phospholipase $A_2$ may also be used but with less efficacy. In another alternative combination, Streptokinase, Plasminogen, DNase or Endonuclease may be used, as well as, DNase or Endonuclease, Phospholipase $A_2$ and Lipase but with even less efficacy. DNase or Endonuclease in combination with Phospholipase $A_2$ is yet another alternative. The efficacy of the three latter combinations was found to be equal.

In accordance with Protocol 3, the enzyme combination is comprised of Streptokinase, Plasminogen, DNase or Endonuclease, Phospholipase $A_2$, and Lipase. Alternatively, enzyme combinations comprising of Streptokinase, Plasminogen, DNase or Endonuclease, and Phospholipase $A_2$ may also be used but with less efficacy. In another alternative combination, Streptokinase, Plasminogen, DNase or Endonuclease may be used with even less efficacy than the latter combination.

Figure 14A:
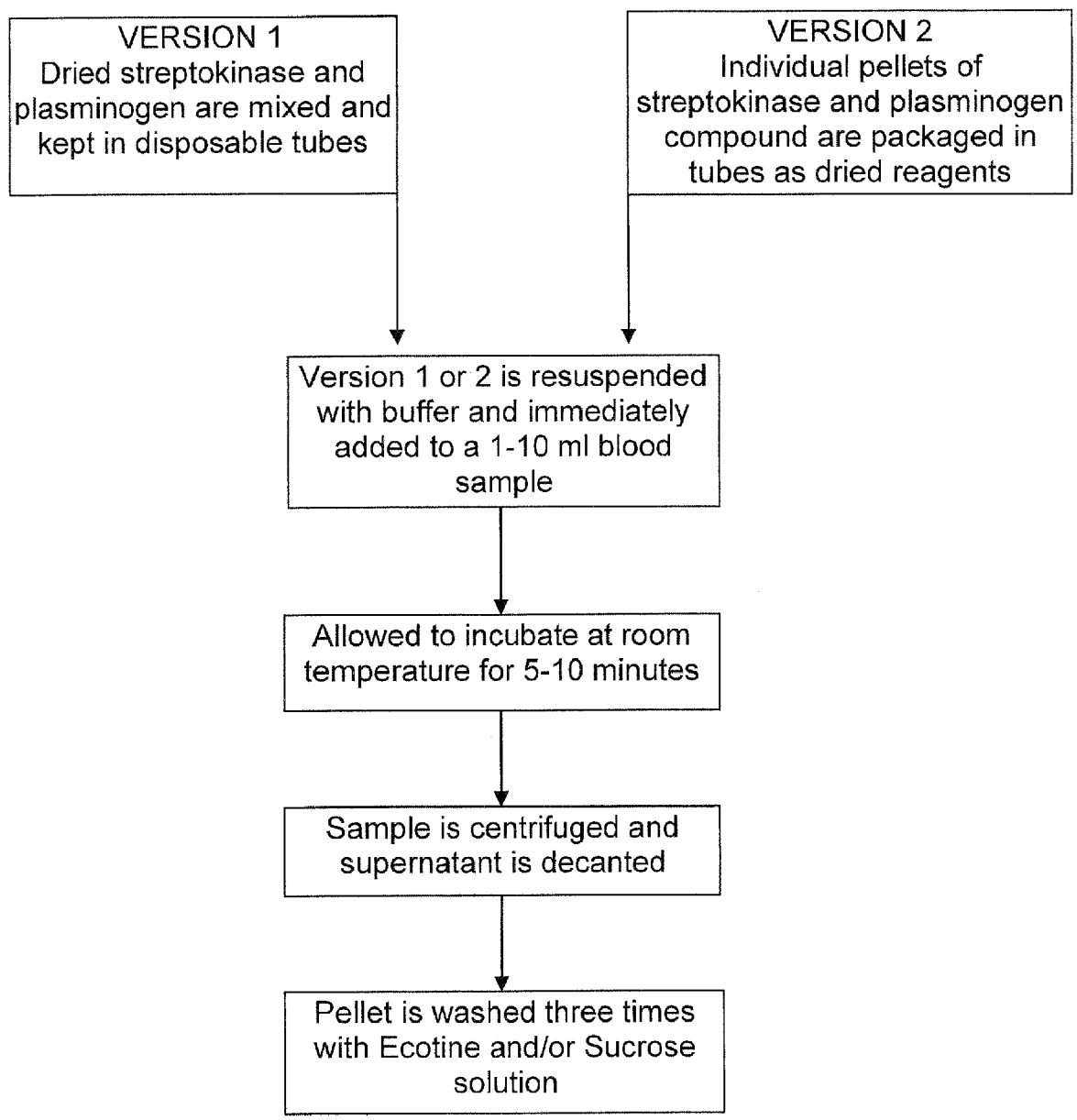
FIG. 14a is a diagrammatic view of the steps of extracting reagents according to Protocol 2 of the invention.
Figure 14B:
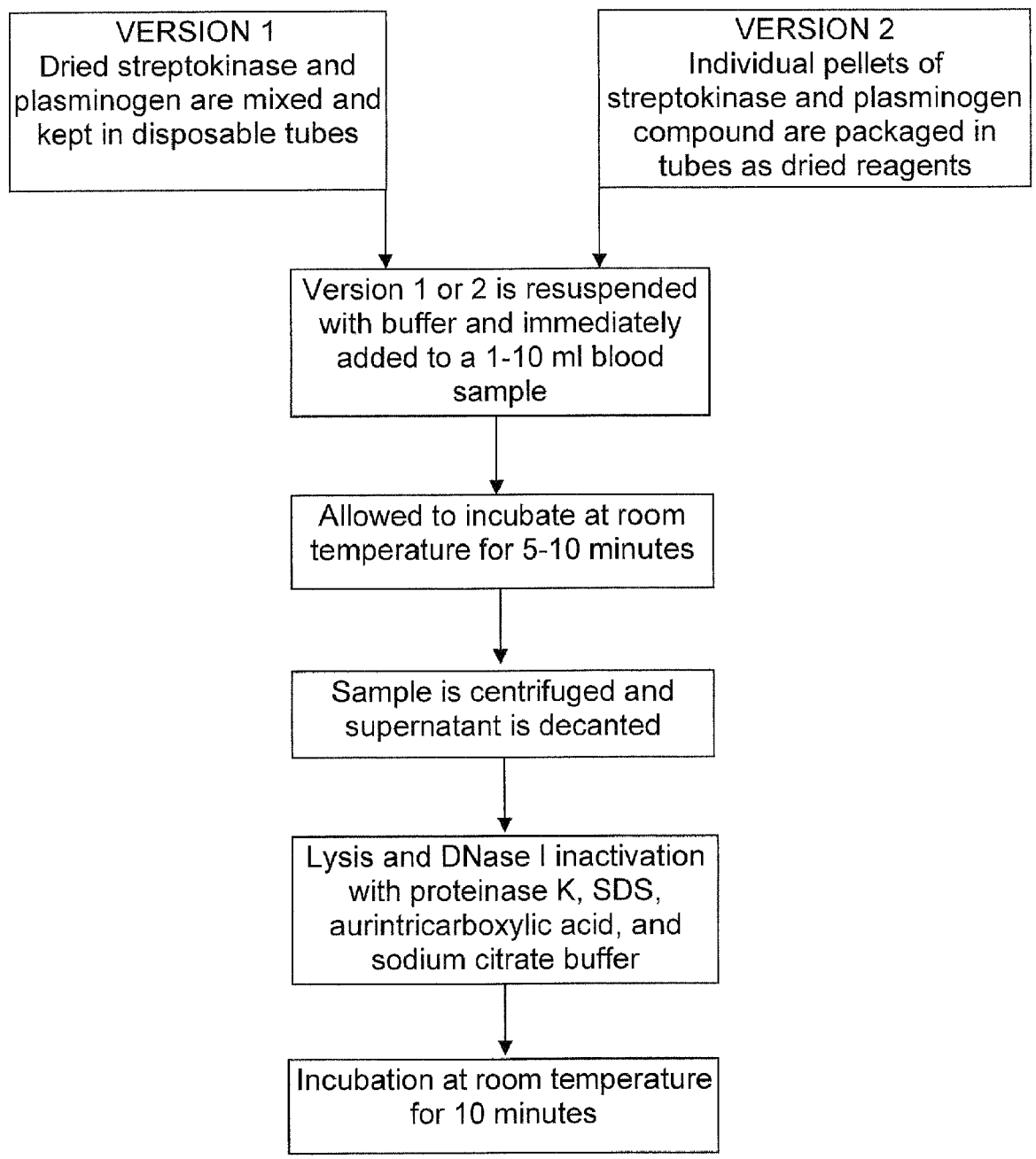
FIG. 14b is a diagrammatic view of the steps of extracting reagents according to Protocol 2 of the invention.

As shown in FIG. 14 with Protocol 2, the sample is centrifuged for a period of 20 minutes at 5,000-5,500×g at a temperature between 10-22° C. after incubation. The supernatant is then decanted and the pellet washed three times with a 10-20 mM solution of Ecotine/20 mM HEPES pH 7.7 and/or a 20-30 mM solution of Sucrose/20 mM HEPES pH 7.7.

Alternatively after incubation, the Protocol 2 sample is centrifuged in similar fashion and the supernatant decanted, followed by sample lysis and DNase or Endonuclease inactivation using 12.5-25 mg Proteinase K, 1-1.5% Sodium Dodecyl Sulfate (SDS), 10-200 mM Aurintricarboxylic Acid and 10-20 mM Sodium Citrate buffer pH 7.8-8.4. The sample is allowed to incubate at room temperature for 10 minutes. The digested sample may then be applied to any commercially available nucleic acid extraction method, shown in FIG. 14b.

Figure 15:
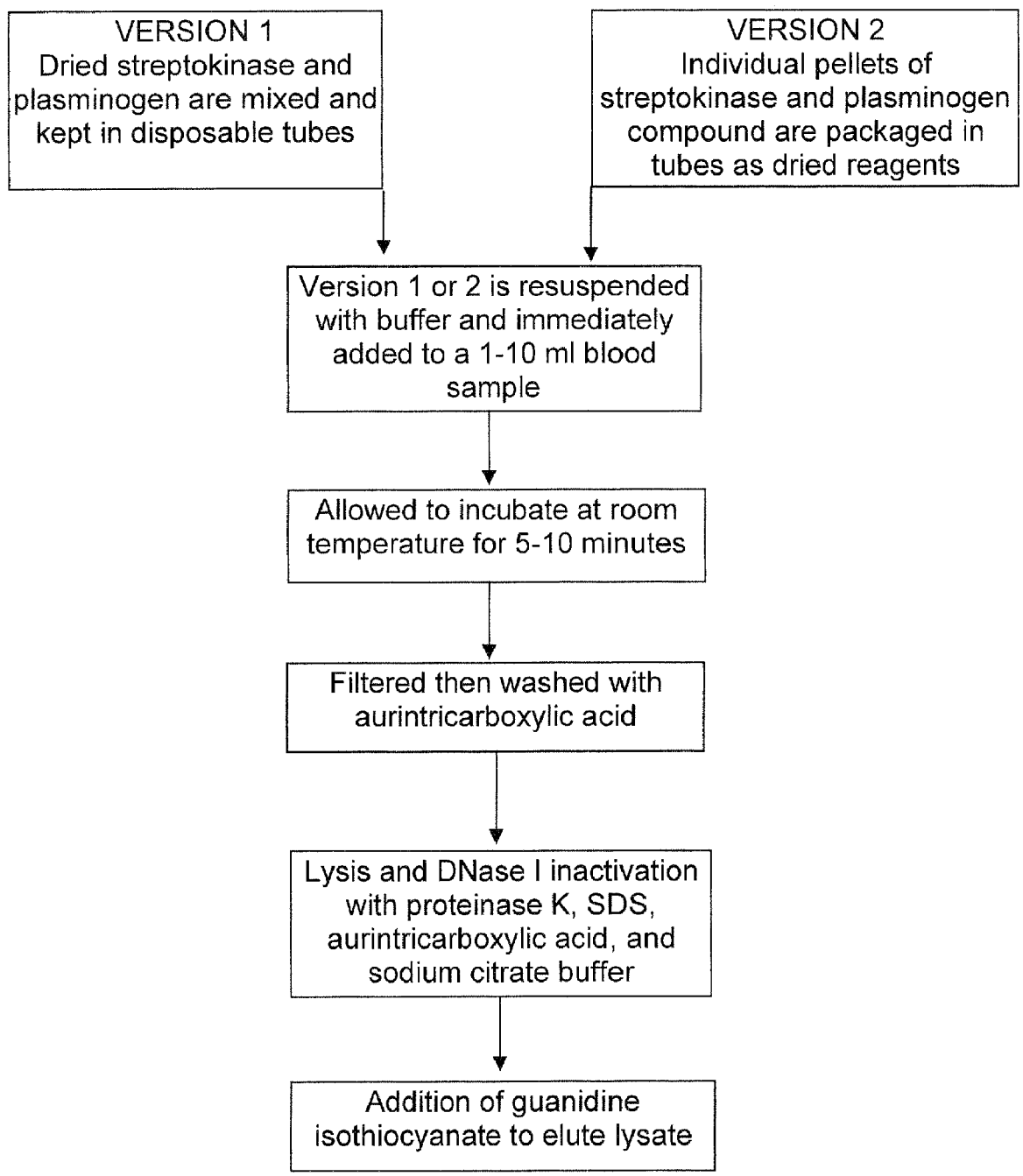
FIG. 15 is a diagrammatic view of the steps of extracting reagents according to Protocol 3 of the invention.

Yet in another alternative, referred to as Protocol 3 and depicted in FIG. 15, the sample is filtered with a 0.22-0.45 μm filter unit and washed with 10-20 ml of 10-200 mM Aurintricarboxylic Acid, followed by sample lysis and DNase or Endonuclease inactivation. Sample lysis and DNase or Endonuclease inactivation is accomplished by using 12.5-25 mg Proteinase K, 1-1.5% SDS, 10-200 mM Aurintricarboxylic acid, and 10-20 mM Sodium Citrate buffer. The sample is then incubated at room temperature for 10 minutes. Addition of 3.5-4.2 M Guanidine Isothiocyanate pH 6.4 is necessary to elute the lysate from the filter surface. The nucleic acid extract may then be further purified using a commercially available method.

Figure 16A:
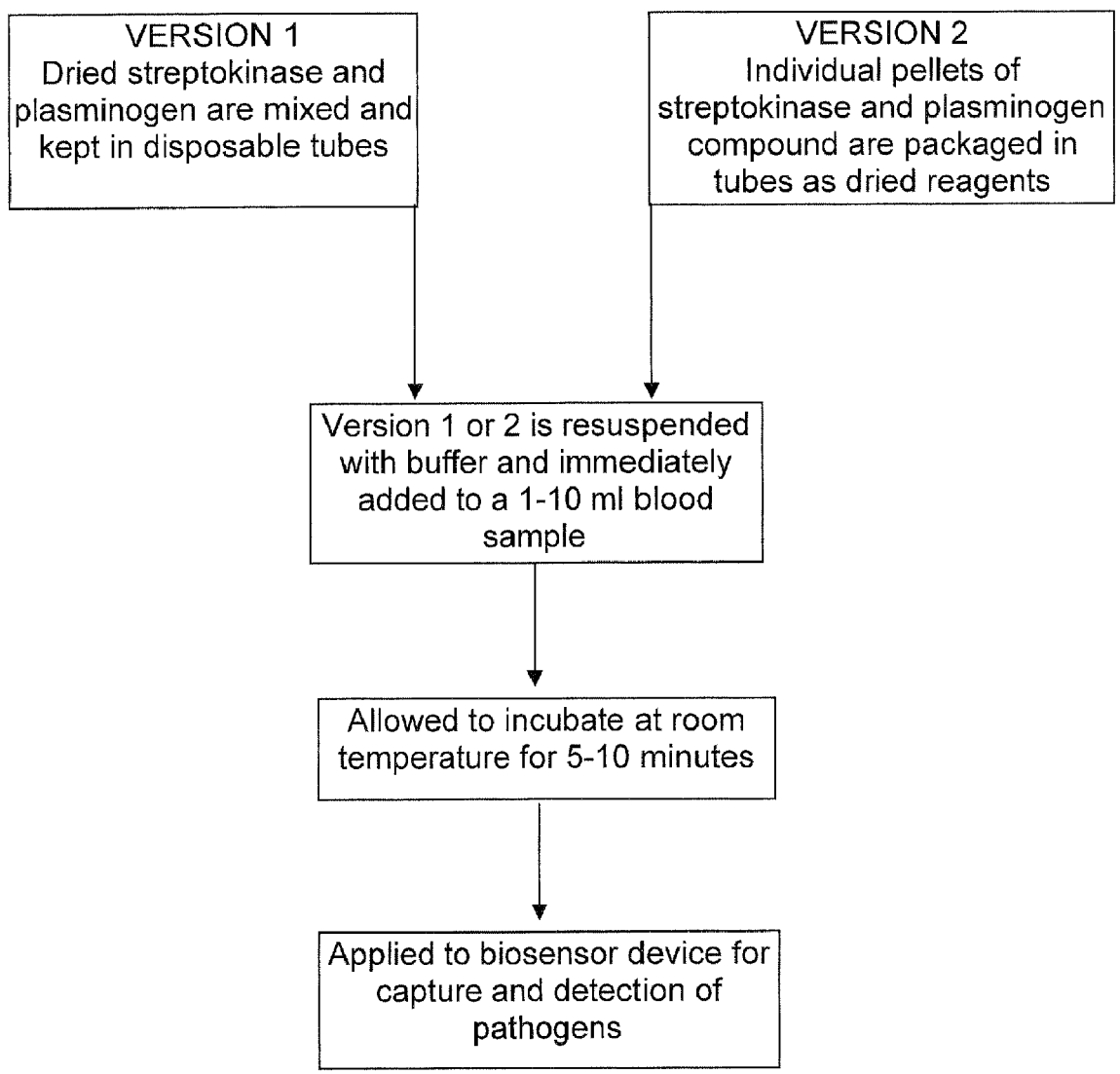
FIG. 16a is a diagrammatic view of the steps of extracting reagents according to Protocol 4 of the invention.

Another alternative, referred to as Protocol 4 and shown as FIG. 16a, applies the sample directly to a biosensor device that will capture and detect bacteria, virus, fungi, toxins, prions, chemical agents, metabolic markers or native disease state markers developed by the patients own body in response to these pathogens and agents present in the blood sample.

Figure 16B:
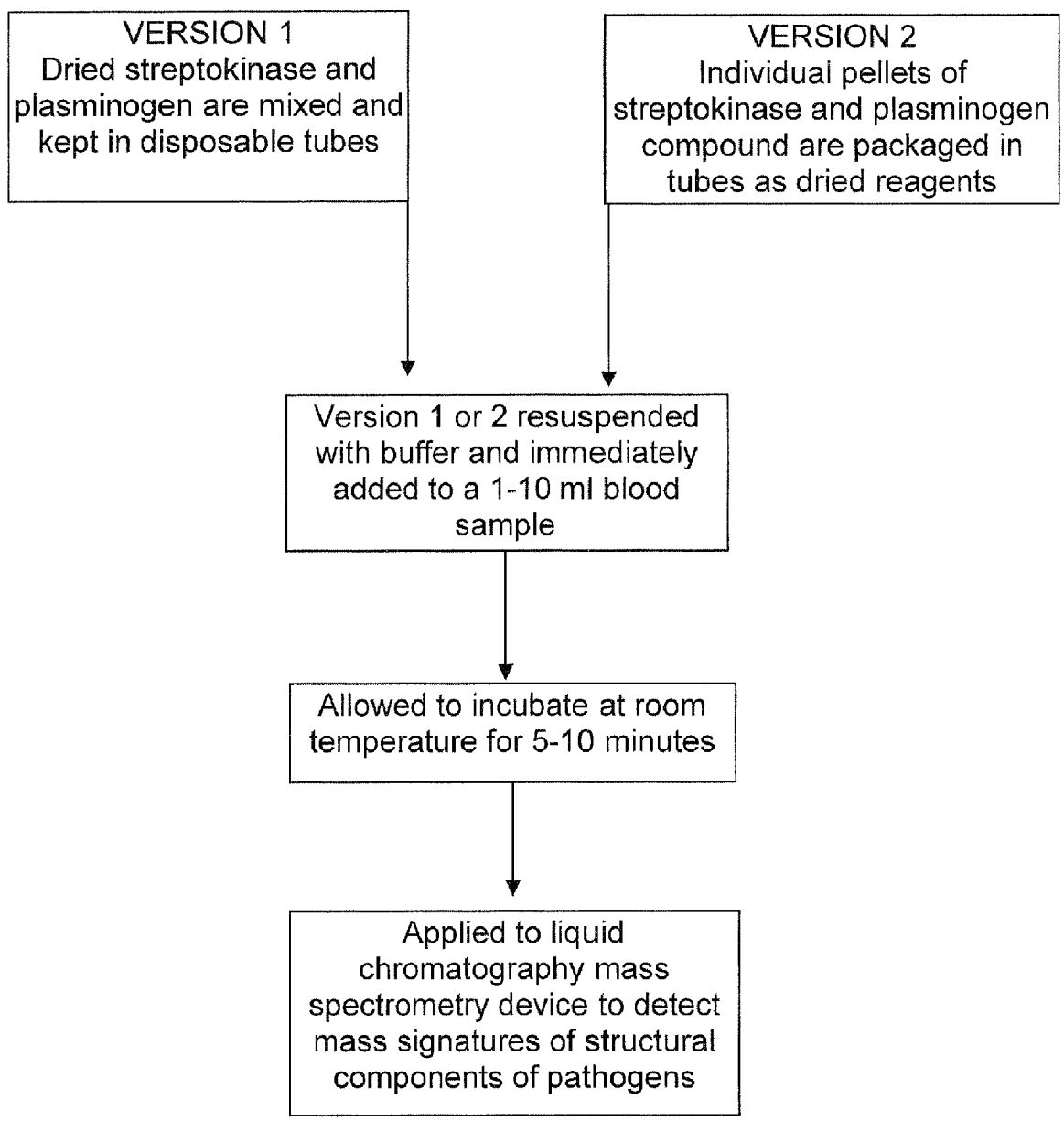
FIG. 16b is a diagrammatic view of the steps of extracting reagents according to Protocol 4 of the invention.

In yet another Protocol 4 alternative shown in FIG. 16b, the sample is applied directly to a liquid chromatography mass spectrometry device that will detect mass signatures of structural components that comprise bacteria, virus, toxins, prions, and chemical agents present in the blood sample or native disease state markers developed by the patients own body in response to these pathogens and agents present in the blood sample.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

The invention claimed is:

1. A method for nucleic acid extraction from a sample comprising aurintricarboxylic acid (ATA) and a chaotropic salt, comprising adding a composition comprising urea and diethylenetriaminepentaacetate (DTPA) to the sample prior to isolation of the nucleic acid, whereby the nucleic acid is freed of ATA.

2. The method according to claim 1, wherein the composition further comprises sodium citrate.

3. The method according to claim 1, wherein the composition further comprises proteinase K.

4. The method according to claim 2, wherein the composition further comprises proteinase K.

5. The method according to claim 1, wherein the composition further comprises methyl 6-O-(N-heptylcarbamoyl)-α-D-glucopyranoside.

6. The method according to claim 1, wherein the composition further comprises ethylenediaminetetraacetate (EDTA).

7. The method according to claim 1, wherein the pH of the sample is brought to about 8.0.

8. The method according to claim 1, wherein the composition further comprises sodium hydroxide.

9. The method according to claim 1, wherein the composition is a dry powder.

10. The method according to claim 1, wherein the concentration of urea in the sample is 6.0 to 7.5M.

11. The method according to claim 1, wherein the sample is subsequently contacted with urease.

12. The method according to claim 11, wherein 1,000 to 100,000 units of the urease are added per ml of sample.

13. The method according to claim 1, which comprises the prior step of heating the solution comprising urea and DTPA to at least 600° C.

14. The method according to claim 13, wherein the urea and DTPA are heated for about 4 hours.

15. The method according to claim 1, wherein the nucleic acid extraction comprises washing and/or binding steps, and the sample is heated to between 55 and 65° C. during the washing and/or binding steps.

16. The method according to claim 1, wherein the sample is blood.

17. The method according to claim 1, wherein the composition further comprises any combination of sodium citrate, proteinase K, methyl 6-O-(N-heptylcarbamoyl)-α-D-glucopyranoside, ethylenediaminetetraacetate (EDTA), and sodium hydroxide.

* * * * *